United States Patent [19]

Klenk et al.

[11] 4,175,188
[45] Nov. 20, 1979

[54] PROCESS FOR THE PRODUCTION OF 1,2,4-TRIAZIN-5-ONE DERIVATIVES

[75] Inventors: Herbert Klenk, Hanau; Werner Schwarze, Frankfurt; Wolfgang Leuchtenberger, Bruchköbel, all of Fed. Rep. of Germany

[73] Assignee: Deutsche Gold- und Silber-Scheideanstalt vormals Roessler, Frankfurt, Fed. Rep. of Germany

[21] Appl. No.: 924,062

[22] Filed: Jul. 12, 1978

[30] Foreign Application Priority Data

Jul. 22, 1977 [DE] Fed. Rep. of Germany ....... 2733180

[51] Int. Cl.² .......................................... C07D 253/06
[52] U.S. Cl. .......................................... 544/182
[58] Field of Search .......................................... 544/182

[56] References Cited

U.S. PATENT DOCUMENTS

| | | | |
|---|---|---|---|
| 4,013,649 | 3/1977 | Bogdanowicz | 260/240 AS |
| 4,057,417 | 11/1977 | Dickore' et al. | 544/182 |
| 4,058,525 | 11/1977 | Hofer et al. | 544/182 |
| 4,058,526 | 11/1977 | Merz et al. | 544/182 |
| 4,113,767 | 9/1978 | Merz | 544/182 |

FOREIGN PATENT DOCUMENTS

2165554 7/1973 Fed. Rep. of Germany .

OTHER PUBLICATIONS

Thesing et al., "Die Chemie der Acylcyanide", Angewandte Chemie, vol. 68, pp. 425–435 (1956).
Ugi et al., Chem. Ber., vol. 94, pp. 1116–1121 (1961).
Ritter et al., J. Amer. Chem. Soc., vol. 70, pp. 4045–4050 (1948).
Hurd et al., J. Amer. Chem. Soc., vol. 66, pp. 2013–2014 (1944).
Dornow et al., Chem. Berichte, vol. 97, pp. 2173–2178 (1964).

Primary Examiner—John M. Ford
Attorney, Agent, or Firm—Cushman, Darby & Cushman

[57] ABSTRACT

1,2,4-triazin-5-one compounds of the general formula (I)

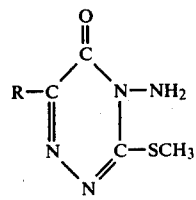

where R is

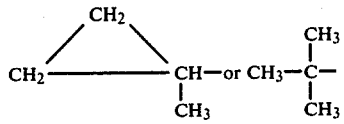

are prepared by reacting a compound of general formula (II)

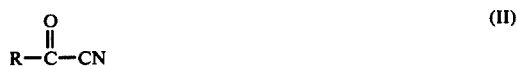

in which R is defined above with either
(a) a tertiary alcohol of general formula (III)

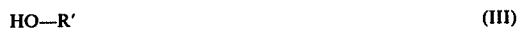

in which R' is a t-alkyl group having 4 to 18 carbon atoms, especially t-amyl or t-octyl or preferably t-butyl or
(b) an alkene of general formula (IV)

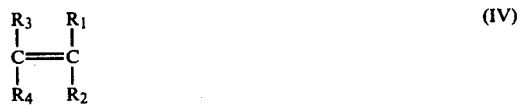

in which $R_1$ and $R_2$ are the same or different and are hydrogen or an alkyl group and $R_3$ and $R_4$ are the same or different and wherein the alkyl groups in each case can be 1 to 15 carbon atoms and wherein preferably $R_1$ and $R_2$ are hydrogen and $R_3$ and $R_4$ each are methyl to form an α-ketocarboxylic acid amide of general formula (V)

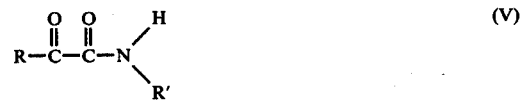

and this, in a given case after previous saponification to the free acid, condensed with thiocarbohydrazide

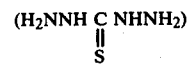

to form a 1,2,4-triazin-5-one compound of general formula (VI)

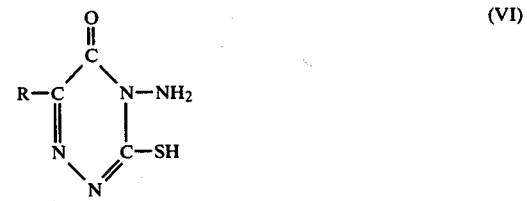

and then the mercapto group is methylated.

34 Claims, No Drawings

PROCESS FOR THE PRODUCTION OF 1,2,4-TRIAZIN-5-ONE DERIVATIVES

BACKGROUND OF THE INVENTION

The object of the invention is to develop a new process for the production of 3-methylmercapto-4-amino-6-t-butyl-1,2,4-triazin-5-one, which is a known herbicide, and for the production of 3-methylmercapto-4-amino-6-(1-methyl-cyclopropyl)-1,2,4-triazin-5-one which has not previously been described and likewise is effective as a selective herbicide. The above-mentioned 6-(1-methyl-cyclopropyl) compound can be used in the same way and against the same plants as the known 6-t-butyl compound also mentioned above.

The 3-methylmercapto-4-amino-6-t-butyl-1,2,4-triazin-5-one can be produced for example according to the process described in German OS No. 2,165,554 by reaction of pivaloyl chloride with an isonitrile, the imidchloride formed hydrolyzed to an α-ketocarboxylic acid amide and the amide further reacted with thiocarbohydrazide in a polar solvent, in a given case in the presence of an acid catalyst. The disadvantage of this process is that it goes circuitously by way of the very ill-smelling and very expensive isonitriles. Besides the 3-mercapto compound can only be obtained in yield of 60% to 79%.

The 1-methyl-cyclopropyl compound set forth above can be used as a herbicide in the manner taught in German OS No. 2,165,554.

SUMMARY OF THE INVENTION

It has now been found that 1,2,4-triazin-5-one compounds of the general formula (I)

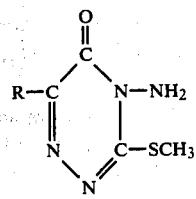

where R is

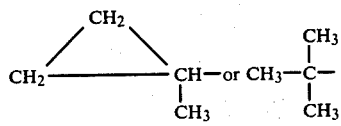

are prepared by reacting a compound of general formula (II)

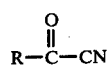

in which R is as defined above with either (a) a tertiary alcohol of general formula (III)

 (III)

in which R' is a t-alkyl group having 4 to 18 carbon atoms, especially t-amyl or t-octyl or preferably t-butyl or (b) an alkene of general formula (IV)

in which $R_1$ and $R_2$ are the same or different and are hydrogen or an alkyl group and $R_3$ and $R_4$ are the same or different and wherein the alkyl groups in each case can be 1 to 15 carbon atoms and wherein preferably $R_1$ and $R_2$ are hydrogen and $R_3$ and $R_4$ each are methyl to form an α-ketocarboxylic acid amide of general formula (V)

and this, in a given case after previous saponification to the free acid, condensed with thiocarbohydrazide

to form a 1,2,4-triazin-5-one compound of general formula (VI)

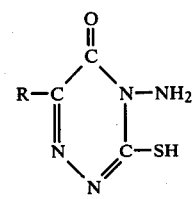

and then the mercapto group is methylated. This procedure avoids the disadvantages of the procedure of German OS No. 2,165,554.

The reaction of the acyl cyanide of general formula (II) with the tertiary alcohol of general formula (III) or the alkene of general formula (IV) takes place under the conditions of the so-called "Ritter Reaction" of "Graf Ritter Reaction" (J.A.C.S. Volume 70, pages 4045 et seq. (1948); J.A.C.S. Volume 70, pages 4048 et seq. (1948); Methodicum Chemicum, Volume 6 (1974)) page 710. It is completely surprising that the quite unstable acyl cyanides are able to carry over this reaction since it was much more to be expected that as a result of the acid treatment there would be a splitting off of hydrocyanic acid.

The reaction can be carried out in the absence of a solvent, but is suitably undertaken in the presence of an organic solvent. Glacial acetic acid and dichloromethane are particularly suitable. Other useful solvents include, for example, higher ethers such as dibutyl ether, diisopropyl ether, dipropyl ether or diamyl ether or acetic anhydride.

The reaction temperature can be varied within wide limits. The preferred temperatures are between −20° C. and +50° C.

Suitable the reactants are added in such amounts that for each mole of acyl cyanide there is employed an overstoichiometrical amount of alcohol or alkene. For example, there can be used per mole of acyl cyanide 1 to 20 moles, preferably 1.5 to 2 moles, of alcohol or alkene.

The acid is also suitably used in a slight excess amount. For example, there can be used per mole of acyl cyanide 1 to 10 moles, preferably 1.1 to 1.5 moles, of acid.

As acid there is preferably used sulfuric acid. However, there can be used other sulfonic acids, e.g., organic sulfonic acids such as benzenesulfonic acid, p-toluene sulfonic acid, methanesulfonic acid, ethanesulfonic acid, etc.

As alcohols of formula III, there can be used for example t-butanol, t-octanol, t-octadecanol, t-dodecanol, t-pentanol, t-hexanol, etc.

As alkenes of formula IV, there can be used particularly 2-methylbutene-2 and diisobutylene and preferably isobutylene. Other alkenes which can be used include 2-methyl-heptadecene-1, 2-ethyl-hexene-1, 3-methyl-hexene-2, 2-methyl-heptene-2, etc.

After the hydrolysis of the reaction mixture, the keto-carboxylic acid amide can be intermediately isolated by known procedures, for example, by crystallization or extraction with subsequent crystallization or distillation.

The acyl cyanide of formula II can be prepared in known manner from the corresponding carboxylic acid halide by reaction with a metal cyanide, e.g., cuprous cyanide (Hurd J.A.C.S. Volume 66, pages 2013-2014 (1944), German patent application No. P 27 08 183.0 and related Klenk U.S. application Ser. No. 802,944, filed June 2, 1977 and now U.S. Pat. No. 4,108,877, German patent application No. P 27 08 182.9 and related Klenk U.S. application Ser. No. 802,942, filed June 2, 1977 and now U.S. Pat. No. 4,108,875. The entire disclosure of Hurd and the two Klenk U.S. applications are hereby incorporated by reference and relied upon.)

The α-ketocarboxylic acid-t-alkylamide of formula V recovered in the first step of the process of the invention can be supplied as such directly to the further reaction with thiocarbohydrazide in the presence of a polar solvent such as an alcohol, e.g., methyl alcohol, ethyl alcohol, isopropyl alcohol or butyl alcohol, water, dimethyl sulfoxide, dimethyl formamide, etc., or mixtures of these solvents and, in a given case, in the presence of an acid catalyst, particularly hydrochloric acid or sulfuric acid, in an amount which is at least equivalent to the amide. Thus, the thiocarbohydrazide can be used in an amount of 1 to 2 moles per mole of the α-ketocarboxylic acid-t-alkylamide. In this reaction, the temperature can be held between 0° C. and the boiling point of the solvent.

However, it is also possible to first convert the α-ketocarboxylic acid-t-alkylamide of formula V to the free α-ketocarboxylic acid which procedure can take place by known methods, and then the ring closure with the thiocarbohydrazide carried out by the methods of A. Dornow (Ber. Volume 97, pages 2173-79 (1964)).

In both cases, the methylation of the sulfur atom is then carried out in known manner, for example, by treating with a methylating agent such as methyl iodide, methyl bromide or dimethyl sulfate in an alkaline medium, e.g., using sodium hydroxide or potassium hydroxide.

The process can comprise, consist essentially of or consist of the steps set forth with the materials set forth.

Unless otherwise indicated, all parts and percentages are by weight.

DESCRIPTION OF THE PREFERRED EMBODIMENTS

Example 1

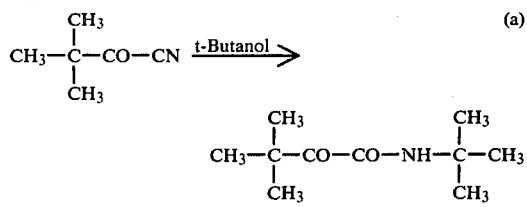

111 grams (1.0 mole) of pivaloyl cyanide were added to a mixture of 148 grams (2.0 moles) of t-butanol and 50 ml of methylene chloride. Then there were dropped in with stirring at 0°-5° C. 150 grams of 98% sulfuric acid and then the temperature increased to 20° C. Stirring was continued for 4 hours, the mixture poured on 400 grams of ice and stirred for 30 minutes. Then the mixture was diluted with 300 ml of methylene chloride, the organic phase separated of and the methylene chloride solution evaporated. There remained a white, crystalline residue which was washed with about 500 ml of water on a suction filter. The residue was then dried. There remained 133 grams (72%) of trimethyl pyruvic acid-N-t-butylamide having a melting point of 63°-65° C.

Analysis Calc: C 64.38; H 10.34; N 7.56. Found: 64.59; 10.44; 7.32.

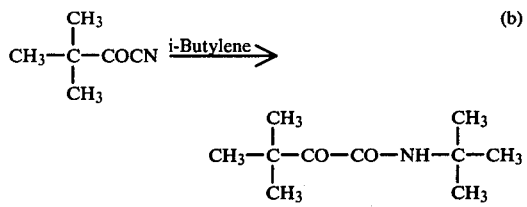

111 grams (1.0 mole) of pivaloyl cyanide were added to a mixture of 150 ml of glacial acetic acid and 150 grams of 100% sulfuric acid. Then there were led in with stirring at 5°-10° C. during 1 hour 112 grams (2.0 moles) of isobutylene. Then the temperature was increased to 20° C. and stirring continued for 2 hours. Then there were dropped in with slight cooling an about 5 normal aqueous NaOH solution until a pH of 8 was reached. Stirring was continued for a further 30 minutes and the precipitated trimethyl pyruvic acid-N-t-butylamide was filtered off. There remained behind 172 grams (93% yield based on the acid cyanide added). The amide had a melting point of 63°-65° C. and is identical with the amide described in (a).

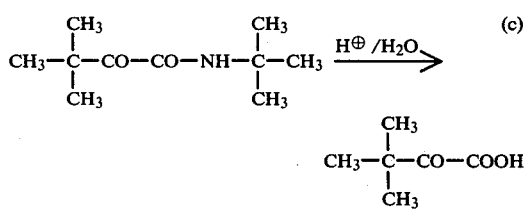

185 grams of trimethyl pyruvic acid-N-t-butylamide were heated in 1 liter of 5 normal HCl for 10 hours under reflux. After cooling the product was extracted by shaking with methylene chloride and then the methylene chloride phase was extracted with dilute aqueous NaOH solution. The alkaline aqueous solution was then adjusted to a pH of 1 with concentrated HCl and then extracted by shaking with ethyl acetate. The ethyl acetate extract was evaporated. There remained behind 97.5 grams (75% of theory) of trimethyl pyruvic acid as a light oil which after some time began to crystallize.

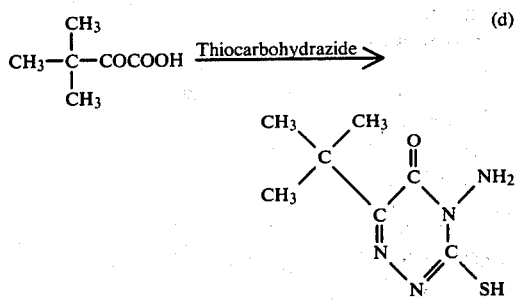

53 grams (0.5 mole) of thiocarbohydrazide in 600 ml of water were heated to boiling. Under stirring there were dropped in during about 2 hours 65 grams (0.5 mole) of the trimethyl pyruvic acid obtained in (c) in ethanol. Then heating was continued for a further 4 hours under reflux. The mixture was allowed to cool and the crystals removed with suction. Thus there were isolated after drying 94 grams (94% of theory of 3-mercapto-4-amino-6-t-butyl-1,2,4-triazin-5-one) (M.P. 212°–214° C.).

(e) Methylation of the 3-mercapto-4-amino-6-t-butyl-1,2,4-triazin-5-one 100 grams of the compound obtained according to (d) were dissolved in a mixture of 250 ml of 2 normal NaOH and 250 ml of methanol and then treated with 75 grams of methyl iodide. Then the mixture was stirred for 4 more hours at 20° C. The reaction product which crystallized out was filtered off with suction, dried and recrystallized from benzene. There were obtained 92 grams (80% of theory) of 3-methylmercapto-4-amino-6-t-butyl-1,2,4-triazin-5-one having a melting point of 126° C.

Example 2

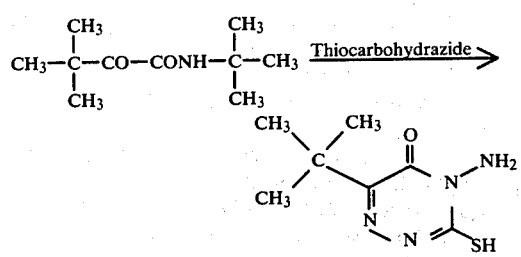

There were dropped into 53 grams (0.5 mole) of thiocarbohydrazide in 500 ml of 1 normal HCl with stirring and heating to reflux 92.5 grams (0.5 mole) of the trimethyl pyruvic acid-t-butylamide produced in accordance with Example 1(a) in 200 ml of ethanol. Then heating was continued for 8 hours. After cooling the mixture was diluted with 1 liter of water and the crystals removed with suction. There were isolated 72 grams (72% of theory) of the desired triazinone (M.P. 209°–213° C.). The methylation was carried out as described in Example 1(e).

Example 3

(a) Production of (1-Methyl-cyclopropyl)-glyoxyltert.-butylamide 109 grams of (1-methyl-cyclopropyl)-carboxylic acid cyanide (1 mole) were added to a mixture of 130 grams of t-butanol and 130 ml of methylene chloride. Then there were dropped in with stirring at 0° to 5° C. 100 grams of 98% sulfuric acid, the temperature increased to 20° C. and stirring continued for 4 hours. Then there were added 18 ml of water and stirring carried out again for 30 minutes. The mixture was diluted with 500 ml of methylene chloride and adjusted with cooling with aqueous NaOH to a pH of 6. The methylene chloride solution was then evaporated. There remained 181 grams (98.9% of theory) of (1-methyl-cyclopropyl)-glyoxyl-tert.-butylamide, M.P. 80° C.

Analysis Calculated: C 65.5; H 9.3; N 7.65. Found: 65.2; 9.4; 7.45.

(b) Production of 4-Amino-6-(1-methyl-cyclopropyl)-3-mercapto-1,2,4-triazin-5-one 183 grams of (1-methyl-cyclopropyl)-glyoxalic acid-tert.-butylamide and 112 grams of thiocarbohydrazide were added to a mixture of 1 liter of 1 normal HCl and 1 liter of ethanol. The mixture was boiled under reflux for 8 hours, cooled, diluted with 2 liters of water and the crystals filtered off with suction. There were obtained white crystals with a yellow luster which were dried.

Amount: 152.6 grams (77.1% of theory)
M.P. 137° to 138° C.

Analysis Calculated: C 42.4; H 5.05; N 28.3; S 16.16. Found: 42.2; 5.1; 28.1; 16.1.

(c) Methylation of the 4-Amino-6-(1-methyl-cyclopropyl)-3-methylthio-1,2,4-triazin-5-one 198 grams of the compound obtained according to (b) were dissolved in 500 ml of 2 normal NaOH and treated with 500 ml of methane and 150 grams of methyl iodide. The mixture was stirred for 6 hours at 20° to 30° C. The crystals formed were filtered off with suction, washed and dried. There are obtained 174.5 grams of final product (dried in a vacuum at 40° C.), white crystals, M.P. 115° to 116° C.

Yield: 82.3% of theory.

| Analysis | Calculated | C 45.3 | H 5.7 | N 26.4 | S 15.1 |
|---|---|---|---|---|---|
| (Molecular weight 212) | Found | 45.3 | 5.8 | 26.1 | 15.3 |

What is claimed is:

1. A process for the production of a 1,2,4-triazin-5-one compound of the formula

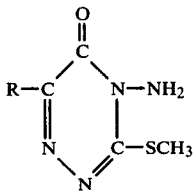

where R is

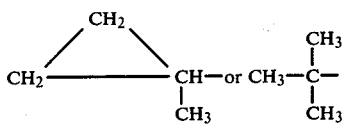

are prepared by reacting under acid conditions an acyl cyanide of the formula

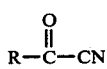

with either
(a) a tertiary alcohol of the formula

in which R' is a t-alkyl group having 4 to 18 carbon atoms or
(b) an alkene of the formula

where $R_1$ and $R_2$ are hydrogen or alkyl and $R_3$ and $R_4$ are alkyl of 1 to 15 carbon atoms
to form an α-ketocarboxylic acid amide of the formula

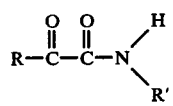

and then either (1) reacting compound (V) with thiocarbohydrazide or (2) saponifying (V) to the free carboxylic acid and condensing the free carboxylic acid with thiocarbohydrazide to form a 1,2,4-triazin-5-one of the formula

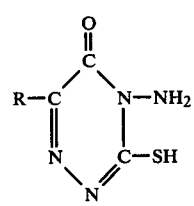

and then methylating the mercapto group.

2. A process according to claim 1 which includes step (1).

3. A process according to claim 2 including compound (a).

4. A process according to claim 3 wherein R' is t-amyl, t-octyl or t-butyl.

5. A process according to claim 4 wherein R' is t-butyl.

6. A process according to claim 3 wherein there is employed 1.5 to 2 moles of compound (III) per mole of acyl cyanide.

7. A process according to claim 3 wherein there are used 1 to 10 moles of acid per mole of acyl cyanide.

8. A process according to claim 7 wherein the acid is sulfuric acid or an organic sulfonic acid.

9. A process according to claim 8 wherein there are used 1.1 to 1.5 moles of acid per mole of acyl cyanide.

10. A process according to claim 9 wherein there are employed 1.5 to 2 moles of compound (III) per mole of acyl cyanide.

11. A process according to claim 8 wherein the methylating agent is methyl bromide, methyl iodide or dimethyl sulfate.

12. A process according to claim 2 wherein R is t-butyl.

13. A process according to claim 2 wherein R is methyl-cyclopropyl.

14. A process according to claim 2 including compound (b).

15. A process according to claim 14 wherein $R_1$ and $R_2$ are both hydrogen and $R_3$ and $R_4$ are both methyl.

16. A process according to claim 15 wherein there are used 1.5 to 2 moles of compound (IV) per mole of acyl cyanide.

17. A process according to claim 14 wherein there are used 1 to 10 moles of acid per mole of acyl cyanide.

18. A process according to claim 17 wherein the acid is sulfuric acid or an organic sulfonic acid.

19. A process according to claim 18 wherein there are used 1.1 to 1.5 moles of acid per mole of acyl cyanide.

20. A process according to claim 19 wherein there are employed 1.5 to 2 moles of compound (IV) per mole of acyl cyanide.

21. A process according to claim 18 wherein the methylating agent is methyl bromide, methyl iodide or dimethyl sulfate.

22. A process according to claim 1 which includes steps (2).

23. A process according to claim 22 including compound (a).

24. A process according to claim 23 wherein R' is t-amyl, t-octyl or t-butyl.

25. A process according to claim 23 wherein there are employed 1.5 to 2 moles of compound (III) per mole of acyl cyanide.

26. A process according to claim 23 wherein there are employed 1 to 10 moles of sulfuric acid or an organic sulfonic acid per mole of acyl cyanide.

27. A process according to claim 26 wherein there are used 1.1 to 1.5 moles of acid per mole of acyl cyanide and 1.5 to 2 moles of compound (III) per mole of acyl cyanide.

28. A process according to claim 22 wherein R is t-butyl.

29. A process according to claim 22 wherein R is methyl-cyclopropyl.

30. A process according to claim 22 including compound (b).

31. A process according to claim 30 wherein $R_1$ and $R_2$ are both hydrogen and $R_3$ and $R_4$ are both methyl.

32. A process according to claim 30 wherein there is used 1 to 10 moles of sulfuric acid or an organic sulfonic acid per mole of acyl cyanide.

33. A process according to claim 32 wherein there are used 1.1 to 1.5 moles of acid per mole of acyl cyanide and 1.5 to 2 moles of compound (IV) per mole of acyl cyanide.

34. A process according to claim 30 wherein there are used 1.5 to 2 moles of compound (IV) per mole of acyl cyanide.

* * * * *